United States Patent [19]

Nitsche

[11] Patent Number: 5,441,737
[45] Date of Patent: Aug. 15, 1995

[54] USE OF APOTRANSFERRIN THAT HAS BOUND ZINC OR COPPER IONS FOR TREATMENT OF TOXIC EFFECTS OF ENDOTOXINS

[76] Inventor: Dietrich Nitsche, Bismarkallee 2, W-2300 Kiel 1, Germany

[21] Appl. No.: 952,861

[22] PCT Filed: Mar. 17, 1992

[86] PCT No.: PCT/DE92/00230
§ 371 Date: Jan. 15, 1993
§ 102(e) Date: Jan. 15, 1993

[87] PCT Pub. No.: WO92/16227
PCT Pub. Date: Oct. 1, 1992

[30] Foreign Application Priority Data

Mar. 21, 1991 [DE] Germany .......................... 41 09 254.6

[51] Int. Cl.$^6$ .................... A61K 31/28; A61K 31/30; A61K 31/315; C07K 103/00
[52] U.S. Cl. ................ 424/193.1; 424/234.1; 424/236.1; 530/350; 530/380; 514/6; 514/8
[58] Field of Search ................ 424/85.8, 94.5, 85.1, 424/193.1, 234.1, 236.1; 530/388.4, 388.26, 350, 380; 514/6, 8

[56] References Cited

U.S. PATENT DOCUMENTS

5,045,466 9/1991 Morrison et al. ............... 435/240.27

OTHER PUBLICATIONS

Osband, M. E. et al., Immunology Today, 11(6):193–195, 1990.
Cross, A. S., et al., Infection and Immunity, 61(7):2741–2747, Jul. 1993.
Biological Abstracts, M. C. McGahan, "Copper and Aspirin Treatment Increase the Antioxidant Activity of Plasma", vol. 90, (1990), Ref. No. 126999.

*Primary Examiner*—David L. Lacey
*Assistant Examiner*—Susan A. Loring
*Attorney, Agent, or Firm*—Herbert W. Larson

[57] ABSTRACT

Apotransferrin bound to zinc or copper is administered to a patient who has endotoxins present in the patient's bloodstream. The apotransferrin improves the elimination of endotoxins from the bloodstream.

1 Claim, No Drawings

USE OF APOTRANSFERRIN THAT HAS BOUND ZINC OR COPPER IONS FOR TREATMENT OF TOXIC EFFECTS OF ENDOTOXINS

BACKGROUND OF THE INVENTION

The invention relates to the use of apotransferrin that has bound divalent zinc or copper ions as an agent for prophylactic and therapeutic treatment of the toxic effects of endotoxins. Apotransferrin is a glycoprotein with an average molecular weight of 80,000 Dalton. It can bind mainly trivalent iron ions reversibly. It can also bind other metal ions instead of iron such as Cu(II), Mn(III), Co(III) or Zn(II). In human and animal organisms, apotransferrin usually occurs as transferrin, a protein-metal complex with trivalent iron.

The main function of apotransferrin is considered to be its ability to bind and transport specific trivalent iron ions, whereby it can bind and transport one or two molecules of iron reversibly. In this way, the iron is transported following its absorption in the small intestine to the iron depots in the liver and spleen as well as in the reticulocytes in the hematopoietic tissue. The normal range of plasma apotransferrin-iron complex (transferrin) concentration is 200 mg/dl to 400 mg/dl.

A further important function of transferrin in its iron-free form is considered to be its bacteriostatic effect (Martin CM, Jandl JH, Finland M. J Infect Dis 1963; 112:158–163; Fletcher J. Immunology 1971; 20:493–500). Iron is an essential growth factor for bacteria. The complexing of iron by transferrin keeps the free iron concentration in the plasma under the minimum required for bacterial growth. Berger und Beger (Berger D, Beger HG. Clin Chim Acta 1987; 163:289–299; Arzneim-Forsch/Drug Res 1988; 38:817–820; and Prog Clin Biol Res 1988; 272:115–124) concluded on the basis of the bacteriostatic effect of transferrin that transferrin in its iron-free form might even fulfil the function of an adjunctive anti-microbial agent in extensive gram-negative infections in the sense of a complement to conventional antibiotic therapy.

Apotransferrin that has bound trivalent iron, i.e. in its form as transferrin, is also capable of reducing the biological activity of endotoxins. The ability of transferrin to neutralize endotoxin increases along with the iron load as is described in detail in DE 38 42 143 and DE 38 44 667. The fact that apotransferrin, having bound iron ions, is more or less capable of neutralizing endotoxins, depending on the iron level, does not necessarily mean that the same effect will achieved when other metal ions are bound.

In contrast to the conclusions described in DE 38 42 143 and in DE 3844 667, Berger et al. report that ". . . the endotoxin binding capacity is restricted to apotransferrin." (Berger D, Winter M, Beger HG. Clin Chim Acta 1990; 189:1 (Summary)) and that the ability of apotransferrin to bind and neutralize endotoxin is reduced when iron is bound (Berger D, Beger HG. Clin Chim Acta 1987; 163:289–299; Arzneim-Forsch/Drug Res 1988; 38:817–820; and Prog Clin Biol Res 1988; 272: 115–124; Langenbecks Archiv fur Chirurgie 1990; Suppl. 1–6; Berger D, Winter M, Beger HG. Clin Chim Acta 1990, 189: p. 1–6). The authors even mention that "transferrin . . . exhibits endotoxicity enhancing activity." (Berger D, Winter M, Beger HG. Clin Chim Acta 1990; 189: p. 4). Berger et al. also report that, besides pH, the presence of divalent cations ($Ca^{2+}$, $Mg^{2+}$, $Mn^{2+}$) in the reaction medium is of decisive importance regarding the binding of endotoxin by apotransferrin (Berger D, Beger HG. Arzneim-Forsch/Drug Res 1988; 38:817–820; Prog Clin Biol Res 1988; 272: 115–124; Berger D, Winter M, Beger HG. Clin Chim Acta 1990, 189: p. 1–6 and Berger D, Kitterer WR, Beger HG. Eur J Clin Invest 1990; 20:66–71). The authors merely mention that divalent cations must be present in the reaction mixture at a concentration of 2 mmol/l or 3 mmol/l ($Mg^{2+}$) and do not describe a potential influence of ion concentration on the binding of endotoxin. The authors do not conclude that an increase in the ion concentration in the solution, and an indirectly related increase in apotransferrin-cation complexes, result in an improvement of endotoxin binding by apotransferrin. Thus these publications contain no indication whatever that a primary binding of cations to apotransferrin could be one of the preconditions for the binding of endotoxins to apotransferrin.

Endotoxin is a constituent of the cellular walls of gram-negative bacteria and is released only by the bacterial decay. It is a macromolecule with a molecular weight of up to $1 \times 10^6$ Dalton, consisting mainly of sugar compounds and fatty acids. It may also include complexed protein residues from the wall of the bacteria. The endotoxin molecule consists of three structurally and immunobiologically different subregions:

Subregion 1, the O-specific chain, consists of several repetitive oligosaccharide units, each of which is made up of a maximum of 5 neutral sugars. The number of oligosaccharides present depends on the strain of bacteria; for example, the endotoxin of S. abortus equi used in our experiments has 8 oligosaccharides in this region.

Subregion 2, the core oligosaccharide, consists, among other things, of n-acetyl-glucosamine, glucose, galactose, heptose and 2-keto-3-desoxyoctone acid.

Subregion 3, The lipid A (MW 2,000 Dalton) consists of a phosphorylated D-glucosamine-disaccharide to which several—approx. 7-long-chain fatty acids are bound as amides and esters. The carrier of the toxic properties is the lipid A, whereby the toxic effects derive from several fatty acid residues in this region.

The size of the endotoxin molecule and its charge characteristics allow for complexing various compounds and proteins with the groups or side-chains of the three subregions in the endotoxin structure without this having any influence on its toxic properties. Normally, there is a protein bound to the lipid A, the so-called lipid A-associated protein. In most cases, separation of this protein component from the lipid A causes no change whatever in the toxic effect in some endotoxins. It was, however, found that binding of proteins onto many endotoxins can also result in a considerable increase in their toxicity (Rietschel E.TH. et al. (1982)): "Bacterial Endotoxins: Chemical Structure, Biological Activity and Role in Septicaemia", Scand. J. Infect. Dis. Suppl. 31: 8–21). For example, it was observed that certain endotoxins that have complexed a certain amount of protein can be 100 times as toxic as endotoxins from which the same protein was separated (Morrison DC, Oudes ZG, Betz J (1980): The role of lipid A and lipid A-associated protein in cell degranulation mechanisms. In: Eaker D. Wadstrom T (Eds). NATURAL TOXINS, pp 287–294, Pergamon Press. New York). In animal experiments as well, a decrease in toxic effect was observed when the protein was split off (Hitchcock PJ, Morrison DC. (1984). "The protein component of bacterial endotoxins". In: E.T. Rietschel (editor) HANDBOOK of ENDOTOXINS, Vol 1: Chemistry of Endotoxin, pp 339–375, Elsevier Science Publishers B.V.).

Free, i.e. biologically active, endotoxin cannot normally be detected in the blood of healthy subjects. In the following pathological conditions, however, increased amounts of biologically active endotoxin may occur in the blood:

a) Increased transfer of endotoxin from the intestinal tract into the blood on account of permeability disturbances in the intestinal wall, e.g. in severe enterocolitis, shock, or increased release in the course of enteral antibiotic therapy.

b) Reduced eliminetion of endotoxins by the liver, e.g. liver dysfunction partial liver resection.

c) Increased endotoxin release from a larger gram-negative focus such as could be found in treatment of peritonitis with antibiotics.

To protect organs from damage, plasma in healthy persons can inactivate the endotoxin that is continually transferred from the intestinal tract. An excessive endotoxin transfer into the blood brings about a rapid exhaustion of endotoxin-inactivating capacity of the plasma, so that even more biologically active endotoxin is found in the plasma, leading to the clinical signs of endotoxemia. If this condition continues, endotoxemia may lead to cell decay, and finally to organ failure. For these reasons, additional therapeutic measures are required to reduce blood endotoxin activity whenever increased endotoxin passage into the blood or reduced hepatic endotoxin elimination are to be expected.

To a certain extent, plasma endotoxin activity can be reduced by administering polyvalent 7S-IgG preparations, presumably due to the lipid A antibodies they contain. A further improvement in endotoxin neutralization is achieved by enriching the IgG preparation with immunoglobulin of the IgM fraction, in which a higher level of lipid A antibody titer is present (Appelmelk BJ et al., Microbiol Pathogenesis 1987; 2: 391–393).

Clinical studies (Baumgartner JD, et al. Prevention of gram-negative shock and death in surgical patients by antibody to endotoxin core glycolipid. Lancet 1985;ii: 59–63; Dunn DL, Priest BP, Condie RM. Protective capacity of polyclonal and monoclonal antibodies directed against endotoxin during experimental sepsis. Arch Surg 1988; 123:1389–1393; Ziegler EJ. et al. Treatment of gram-negative bacteremia and septic shock with HA-1A human monoclonal antibody against endotoxin. N Engl J Med 1991, 324: 429–436) have demonstrated that lethality of septicemia can be reduced by decreasing plasma endotoxin activity if monoclonal antibodies to the core or the lipid A portion of the endotoxin are administered.

An alternative to the neutralization of endotoxin by monoclonal antibodies is neutralization of the toxic effect of endotoxin by transferrin (DE 38 44 667). The combination of transferrin with polyvalent immunoglobulin preparations can achieve a synergistic effect as described in DE 38 42 143.

As described in E 38 44 667 in detail, the capacity of apotransferrin to neutralize endotoxin increases as the content of trivalent iron ions increases. In the organism, however, the iron can be split off from the transferrin by means of a reduction to $Fe^{2+}$. Since the oxygen activation of enzyme-coupled reactions, i.e. formation of oxygen radicals by neutrophil granulocytes, can be stimulated by an increased presence of $Fe^{2+}$ ions, it is possible that transferrin therapy may facilitate the undesirable formation of harmful oxygen radicals in the organism. However, non-enzymatic processes that lead to oxygen activation and the damaging oxygen radicals it entails, such as the so-called Haber-Weiss reaction (Haber F., Weiss J. Proc Royal Soc [A]1934; 147: 332–351) may be catalysed by the reduced divalent iron split off from transferrin (Carlin G., Djursäter R. FEBS Lett 1984; 177: 27–30). The raised plasma protease activity in septicemia is another factor that can lead to a splitting of the transferrin molecule (Esparza I., Brock JH. Biochem Biophys Acta 1980; 622:297–304; Doring GM. et al. Infect Immun 1988; 56: 291–293). The transferrin fragments that are released in this way and have complexed iron can also catalyze oxygen radical formation by neutrophil granulocytes (Bradley EB., Edeker BL. J Clin Invest 1991; 88: 1092–1102). The oxygen radicals can, on the one hand, cause direct damage to the cell membrane; on the other hand, they may damage the organism indirectly by increasing prostaglandin synthesis.

SUMMARY OF THE INVENTION

It is the object of this invention to provide a therapeutic agent suitable as a means of controlling the biological effects of endotoxin to a sufficient degree by virtue of its ability to neutralize large amount of endotoxin and thus suitable for use as an efficient agent for prophylactic and therapeutic treatment of the toxic effects of endotoxins. The agent should also be capable of minimizing the undesirable formation of harmful oxygen radicals in endotoxemia.

The invention thus provides for the use of apotransferrin that has bound divalent zinc or copper ions. These apotransferrin-metal complexes are also suitable for combination with immunoglobulin preparations or addition to a plasma protein solution or a serum preserve.

DETAILED DESCRIPTION OF THE INVENTION

In vitro and in vivo experiments were carried out to test the capacity of the complexes of apotransferrin with divalent zinc or copper ions as well as the combination of these complexes with immunoglobulins to inactivate endotoxins.

In vitro experiments:

A) Quantitative investigations of influence of transferrin-metal complexes on biological activity:

Apotransferrin-zinc and apotransferrin-copper as well as each of these combined with immunoglobulins were incubated with increasing amounts of endotoxin at 37° C. for 60 minutes. Following incubation, quantitative determination of the biological activity of endotoxin in the supernatant was carried out with a modification of the Limulus test using a chromogenic substrate (Nitsche et al. In: Watson SW, Levin J, Novitsky TJ (eds.) DETECTION OF BACTERIAL ENDOTOXINS WITH THE LIMULUS AMEBOCYTE LYSATE TEST, pp. 417–429 (1987)). The lower detection limit in this modified version of the Limulus test is 1 EU/dl. The endotoxin activity measured by the Limulus test corresponds to the biological activity of the endotoxin (Nitsche D, Ulmer A., Flad HD: Endotoxin determination by the Limulus test and the biological activity of endotoxin. Does a correlation exist?—in preparation). Experiments carried out prior to the endotoxin measurements did not reveal any influence on the Limulus reaction by $Zn^{2+}$ or $Cu^{2+}$ ions.

The apotransferrin used in the experiments was nearly free of metal ions (Atf.-O). No zinc was detected in this apotransferrin (Atf.-O) by means of atomic absorption spectroscopy. No copper was found in the samples, either. The iron assay method described by Megraw and Bouda (Megraw RE, Hritz AM, Babson AL and Carroll JJ (1973) Clin. Biochem. 6: 266; Bouda J (1968) Clin. Chem. Acta 21:159) revealed no iron content in the 5% solution of apotransferrin. The lower detection limit of this method is 0.3 µg/dl. Various amounts of zinc chloride ($ZnCl_2$) were added to the apotransferrin (Atf.-O) to obtain apotransferrin-zinc solutions with a zinc content of 4.8 µg/g of apotransferrin (Atf.-Zn(A)) as well as apotransferrin with a zinc content of 598 µg/g of apotransferrin (Atf.-ZnB)).

Various amounts of copper(II) chloride ($CuCl_2$) were added to the apotransferrin (Atf.-O) to obtain apotransferrin-copper solutions with a copper content of 57 µg/g of apotransferrin (Atf.-Cu(A)) as well as apotransferrin-copper with a copper content of 740 µg/g of apotransferrin (Atf.-Cu(B)).

Apotransferrin-iron was used as reference. Iron(III) chloride ($FeCl_3$) was added to apotransferrin (Atf.-O) so as to produce an apotransferrin-iron solution with an iron content of 598 µg of iron per gram of transferrin.

The following immunoglobulin preparations were used: 7S IgG (Sandoglobin$^R$) as well as 7S IgG enriched with 12% IgM (IgG/A/M=Pentaglobin$^R$).

Endotoxins from the following bacterial strains were used: Salmonella abortus equi (NOVOPYREXAL$^R$), Pseudomonas aeruginosa Fisher type 7, as well as the FDA endotoxin standard von E.coli O113:H10:KO.

DETERMINATION OF THE "MEAN PERCENTAGE OF INACTIVATION"

The percentage of endotoxin inactivated in each case was calculated from the difference between the initial added endotoxin concentration and the endotoxin activity measured following incubation with the protein. The "mean percentage of inactivation" for each protein concentration for the entire range of endotoxin concentrations tested (10 EU/dl–1000 EU/dl) was calculated on the basis of the values determined in this way for the 45 different endotoxin concentrations tested.

DETERMINATION OF ENDOTOXIN INACTIVATION CAPACITY

In order to quantify the capacity of apotransferrin-copper, apotransferrin-zinc and apotransferrin-iron as well as the combination of apotransferrin-zinc and apotransferrin-copper with immunoglobulins to inactivate endotoxin, the "INACTIVATION CAPACITY" was determined. To improve measurement precision, this parameter was not determined at equivalence, but rather at endotoxin excess concentrations of 10 EU/dl and 100 EU/dl. This parameter was calculated on the basis of the amount of endotoxin (EU/dl) that had to be added to each protein preparation to reach a concentration of free endotoxins of 10 EU/dl or 100 EU/dl in the supernatant following incubation (60 minutes, 37° C.) with the protein preparation. This endotoxin concentration was calculated for each preparation (apotransferrin-zinc, apotransferrin-copper, immunoglobulin and the combination of apotransferrin-zinc and apotransferrin-copper with immunoglobulin) on the basis of the relation between the amount of endotoxin added and the endotoxin concentration measured in the supernatant following incubation. The inactivation capacity was determined by a series of measurements in which endotoxin in increasing concentrations (10 EU/dl, 25 EU/dl, 50 EU/dl, 100 EU/dl, 200 EU/dl, 300 EU/dl, 500 EU/dl, 750 EU/dl and 1,000 EU/dl) was incubated for 60 minutes together with the various protein preparations. The concentration of apotransferrin-zinc or apotransferrin-copper in the reaction preparation was 312.5 mg/dl. Measurements carried out with the combination of apotransferrin-zinc or apotransferrin-copper with immunoglobulin, the concentration of each protein component in the reaction mixture was 312 mg/dl.

The mean endotoxin concentration that can be inactivated by each protein preparation [mg/dl] under the given conditions is the amount of endotoxin determined in this way minus the given amount of excess endotoxin (10 EU/dl or 100 EU/dl). In relation to a protein concentration of 100 mg/dl, this amount of endotoxin is a gauge of the "mean inactivation capacity (EU/100 mg)" of each apotransferrin-metal complex or combination of an apotransferrin-metal complex with immunoglobulin.

RESULTS

1.) APOTRANSFERRIN-METAL COMPLEX:

When endotoxin is incubated with apotransferrin free of metal ions (Atf.-O), an average reduction in endotoxin activity of 32.2% to 43.6% is registered, depending on the type and concentration of endotoxin.

When endotoxin is incubated with apotransferrin-zinc (Atf.-Zn(A)) with a zinc content of 4.8 µg/g of apotransferrin, an average reduction in endotoxin activity of 72.5% to 82.4% is registered, depending on the type and concentration of endotoxin.

When endotoxin is incubated with apotransferrin-zinc (Atf.-Zn(B)) with a zinc content of 598 µg/g of apotransferrin, a reduction in endotoxin activity of 91.4% to 97.8% is registered, depending on the type and concentration of endotoxin.

When endotoxin is incubated with apotransferrin-copper (Atf-Cu(A)) with a copper content of 57 µg/g of apotransferrin, an average reduction in endotoxin activity of 84% to 89.3% is registered, depending on the type and concentration of endotoxin.

When endotoxin is incubated with apotransferrin-copper (Atf.-Cu(B)) with a copper content of 740 µg/g of apotransferrin, a reduction in endotoxin activity of 90.8% to 96.7% is registered, depending on the type and concentration of endotoxin.

When endotoxin is incubated with apotransferrin-iron (Trf.-Fe) with an iron content of 598 µg/g of apotransferrin, an average reduction in endotoxin activity of 92.2% to 97.6% is registered, depending on the type of endotoxin and the amount added.

a) On the basis of an endotoxin excess of 10 EU/dl, the inactivation capacity is:
  I.) Atf.-O: For S.abortus equi 1.8 EU/100 mg, for E.coli 2.3 EU/100 mg and for Pseudomonas aeruginosa 2.7 EU/100 mg.
  II.) Atf.-Zn(A): For S.abortus equi 11.1 EU/100 mg, for E. coli 16.3 EU/100 mg and for Pseudomonas aeruginosa 14.9 EU/100 mg.
  III.) Atf.-Zn(B): For S.abortus equi 66.8 EU/100 mg, for E. coli 87.02 EU/100 mg and for Pseudomonas aeruginosa 72.49 EU/100 mg.

IV.) Atf.-Cu(A): For S.abortus equi 34.6 EU/100 mg, for E. coli 43.8 EU/100 mg and for Pseudomonas aeruginosa 39.7 EU/100 mg.

V.) Atf.-Cu(B): For S.abortus equi 70.1 EU/100 mg, for E. coli 79.4 EU/100 mg and for Pseudomonas aeruginosa 64.6 EU/100 mg.

VI.) Trf.-Fe: For S.abortus equi 76.7 EU/100 mg, for E. coli 78.2 EU/100 mg and for Pseudomonas aeruginosa 73.8 EU/100 mg.

b) On the basis of an endotoxin excess of 100 EU/dl, the inactivation capacity is:

I.) Atf.-0: For S.abortus equi 17.8 EU/100 mg, for E.coli 19.4 EU/100 mg and for Pseudomonas aeruginosa 20.6 EU/100 mg.

II.) Atf,-Zn(A): For S.abortus equi 109.7 EU/100 mg, for E.coli 137.4 EU/100 mg and for Pseudomonas aeruginosa 145.5 EU/100 mg.

III.) Atf.-Zn(B): For S.abortus equi 507.6 EU/100 mg, for E. coli 578.5 EU/100 mg and for Pseudomonas aeruginosa 647.3 EU/100 mg.

IV.) Atf.-Cu(A): For S.abortus equi 362 EU/100 mg, for E. coli 387.4 EU/100 mg and for Pseudomonas aeruginosa 409 EU/100 mg.

V.) Atf.-Cu(B): For S.abortus equi 522.4 EU/100 mg, for E. coli 527 EU/100 mg and for Pseudomonas aeruginosa 585.1 EU/100 mg.

VI.) Trf.-Fe: For S.abortus equi 418.7 EU/100 mg, for E. coli 571.1 EU/100 mg and for Pseudomonas aeruginosa 643.9 EU/100 mg.

2.) APOTRANSFERRIN-METAL COMPLEX and 7S IgG: The combination of apotransferrin-zinc or apotransferrin-copper with a 7S IgG preparation improves inactivation of endotoxin. Incubation of endotoxin with apotransferrin (312 mg/dl) and 7S IgG reduces endotoxin activity by a maximum of 61% to 68% at endotoxin concentrations under 100 EU/dl when apotransferrin (Atf.-0) is used that is free of zinc, copper and iron. In the endotoxin concentration range above 100 EU/dl, this combination reduces endotoxin activity by only 47.1% to 54.9%.

When apotransferrin-zinc (Atf.-Zn(A)) with a zinc content of 4.8 µg of zinc per gram of apotransferrin is used in combination with the 7S IgG preparation, a reduction in endotoxin activity of 83.1% to 89.1% is registered, depending on the concentration and the type of endotoxin used.

When apotransferrin-zinc (Atf.-Zn(B)) with a zinc content of 598 µg per gram of apotransferrin is used in combination with the 7S IgG preparation, endotoxin activity is reduced by 94.4% to 97.8%, depending on the concentration and the type of endotoxin.

When apotransferrin copper(Atf.-Cu(A)) with a copper content of 57 µg per gram of apotransferrin is used in combination with 7S IgG, endotoxin activity is reduced by 87.2% to 93.1%, depending on the concentration and the type of endotoxin.

a) On the basis of an endotoxin excess of 10 EU/dl, the inactivation capacity is:

I.) Atf.-0 and 7S IgG: For S.abortus equi 6.1 EU/100 mg, for E.coli 10.6 EU/100 mg and for Pseudomonas aeruginosa 11.4 EU/100 mg.

II.) Atf.-Zn(A) and 7S IgG: For S.abortus equi 24.2 EU/100 mg, for E. coli 30.1 EU/100 mg and for Pseudomonas aeruginosa 27.5 EU/100 mg.

III.) Atf.-Zn(B) and 7S IgG: For S.abortus equi 74.1 EU/100 mg, for E. coli 98.9 EU/100 mg and for Pseudomonas aeruginosa 86.8 EU/100 mg.

IV.) Atf.-Cu(A) and 7S IgG: For S.abortus equi 40.1 EU/100 mg, for E. coli 50.6 EU/100 mg and for Pseudomonas aeruginosa 46.3 EU/100 mg.

b) On the basis of an endotoxin excess of 100 EU/dl, the inactivation capacity is:

I.) Atf.-0 and 7S IgG: For S.abortus equi 28.6 EU/100 mg, for E.coli 30.7 EU/100 mg and for Pseudomonas aeruginosa 39.1 EU/100 mg.

II.) Atf.-Zn(A) and 7S IgG: For S.abortus equi 151.5 EU/100 mg, for E. coli 177.9 EU/100 mg and for Pseudomonas aeruginosa 195.5 EU/100 mg.

III.) Atf.-Zn(B) and 7S IgG: For S.abortus equi 538.4 EU/100 mg, for E. coli 602.7 EU/100 mg and for Pseudomonas aeruginosa 675.1 EU/100 mg.

IV.) Atf.-Cu(A) and 7S IgG: For S.abortus equi 554.7 EU/100 mg, for E. coli 547.3 EU/100 mg and for Pseudomonas aeruginosa 608.1 EU/100 mg.

3.) APOTRANSFERRIN-ZINC and IgG/A/M (12% IgM): The addition of apotransferrin-zinc to an IgG preparation enriched with IgA and 12% IgM (IgG/A/M) causes a further improvement in inactivation capacity. When endotoxin is incubated with the combination of IgG/A/M (12% IgM) (312 mg/dl) and apotransferrin-zinc (Atf,-Zn(A) (312 mg/dl) with a zinc content of 4.8 µg is used, endotoxin activity is reduced by 84 7% to 92 6% depending on the concentration and the type of endotoxin.

When IgG/A/M (12% IgM) (312 mg/dl) is combined with apotransferrin-zinc (Atf.-Zn(B) (312 mg/dl) with a zing content of 598 µg, endotoxin activity is reduced by 94.8 to 98.1%, depending on the concentration and the type of endotoxin.

a) On the basis of an endotoxin excess of 10 EU/dl, the inactivation capacity is:

I.) Atf.-Zn(A) and IgG/A/M: For S.abortus equi 26.9 EU/100 mg, for E.coli 31.5 EU/100 mg and for Pseudomonas aeruginosa 24.9 EU/100 mg.

II.) Atf.-Zn(B) and IgG/A/M: For S.abortus equi 93.8 EU/100 mg, for E. coli 108.5 EU/100 mg and for Pseudomonas aeruginosa 97.8 EU/100 mg.

b) On the basis of an endotoxin excess of 100 EU/dl, the inactivation capacity is:

I.) Atf.-Zn(A) and IgG/A/M: For S.abortus equi 141.1 EU/100 mg, for E.coli 173.2 EU/100 mg and for Pseudomonas aeruginosa 192.5 EU/100 mg.

II.) Atf.-Zn(B) and IgG/A/M: For S.abortus equi 688 EU/100 mg, for E. coli 828 EU/100 mg and for Pseudomonas aeruginosa 796.9 EU/100 mg.

B) Influence on release of the mediators ILi and IL 6

The release of IL 1 and IL 6 from monocytes was used as an additional parameter for the degree of inactivation of the biological activity of the endotoxins by the complexes of divalent zinc ions with apotransferrin. Endotoxin was incubated with apotransferrin-zinc or with the combination of apotransferrin-zinc and immunoglobulin (60 min., 37°). The supernatant was then incubated with monocytes and the concentration of the mediators interleukin 1 and interleUkin 6 released by the monocytes was measured in the supernatant. Apotransferrin-zinc (Atf.-Zn(A)) with a zinc content of 4.8 µg per gram of apotransferrin as well as apotransferrin-zinc (Atf.-Zn(B)) with a zinc content of 598 µg per gram of apotransferrin were used.

The following immunoglobulins were used: 7S IgG (IgG/A/M) enriched with 12% IgM (Pentaglobin).

Endotoxins from the following bacterial strains were used: Salmonella abortus equi (NOVOPYREXAL$^R$)

and the FDA endotoxin standard EC-5 from E. coli 0113:H10:K0.

Apotransferrin-zinc and apotransferrin-zinc in combination with immunoglobulin were incubated together with endotoxin at 37° C. for 60 minutes. Heat-denatured 7S IgG (80°, 10 min.) with an identical zinc content in each case (4.6 μg or 598 μg of zinc/g of 7S-IgG) was used as a reference protein. The concentration of proteins in the preparations was 312 mg/dl respectively. Incubation was carried out with endotoxin concentrations of from 50 EU/dl to 500 EU/dl.

Following incubation, each endotoxin solution was incubated with mononuclear cells from healthy donors (16 hours at 37° C.). Then the concentration of the released mediators IL 1 and IL 6 was determined. IL 1 was measured by means of the fibroblast proliferation test (Loppnow, H.; Flad, H.-D.; Ulmer, A.-J. et al. "Detection of Interleukin 1 with Human Dermal Fibroblasts" Immunbiol., 1989, 179, 283–291) using an EL4-6.1 thymoma cell line. The Concentration of IL 6 was also determined by means of a proliferation test using an IL 6-dependent murine hybridoma (7TD1) (Van Damme J. Cayphas S. et al. (1987) Eur. J. Biochem. 168: 543–550; as well as Van Oers MHJ. Van der Heyden A. and Aarden LA. (1988) Clin. exp. Immunol. 71: 314–419).

RESULTS

The incubation of endotoxin with apotransferrin-zinc resulted in a reduction in the endotoxin-induced release of mediators from the mononuclear cells. This effect is dependent on the zinc load of the apotransferrin—it can be improved by raising the zinc content. Combining apotransferrin-zinc with immunoglobulins further intensifies the inhibitive effect of the apotransferrin-zinc complex on the release of mediators.

I.) REFERENCE PROTEIN (heat-inactivated 7S IgG)

Following incubation of endotoxin (500 EU/dl) with heat-inactivated 7S IgG to which zinc had been added, and which was used as the reference protein, no difference in the amount of mediators released was determined between the reference protein with a zinc content of 4.6 μg per g (Zn(A)) and the reference protein with a zinc content of 598 μg per g (Zn(B)). IL-1: Following incubation of the reference protein with endotoxin from S. abortus equi, the mean release of IL-1 was 2,685 U/ml; following incubation with endotoxin from E. coli IL-1 release was 2,968 U/ml. IL-6: Following incubation of the reference protein with endotoxin from S. abortus equi, the mean release of IL-6 was 3,621 U/ml; following incubation with endotoxin from E. coli IL-6 release was 5,974 U/ml.

II.) APOTRANSFERRIN-ZINC a) Following incubation of 500 EU/dl of endotoxin with Atf.-Zn(A) the average release of IL1 was 321 U/ml with S. abortus equi and 412 U/ml with E. coli. Average release of IL6 following incubation with apotrans-ferrin-zinc (Atf.-Zn(A)) was 1,132 U/ml with endotoxin from S. abortus equi and 1,825 U/ml with E. coli endotoxin.

b) Following incubation of 500 EU/dl of endotoxin with Atf.-Znf(B) the average release of IL 1 was 102 U/ml with S. abortus equi and 47 U/ml with E. coli. Average release of IL6 following incubation with apotrans-ferrin-zinc (Atf.-Zn(B)) was 526 U/ml with endotoxin from S. abortus equi and 316 U/ml with E. coli endotoxin.

III.) APOTRANSFEPaIN-ZINC and IgG/A/M (12% IgM)

The combination of apotransferrin-zinc with a 7S IgG preparation enriched with IgA and 12% IgM (IgG/A/M) had the following results at an immunoglobulin concentration of 312 mg/dl—and an apotransferrin-zinc concentration of 312 mg/dl as well—after incubation with 500 EU/dl of endotoxin:

a) With the combination of IgG/A/M with Atf.-Zn(A) the average release of IL 1 was 227 U/ml with endotoxin from S. abortus equi and 267 U/ml with endotoxin from E. coli. Release of IL 6 following incubation was 872 U/ml with endotoxin from S. abortus equi and 631 U/ml with E. coli endotoxin.

b) With the combination of IgG/A/M (12%) with Atf.-Zn(B) the average release of IL 1 was 31 U/ml with endotoxin from S. abortus equi and 17 U/ml with endotoxin from E. coli. Average release of IL6 following incubation under these conditions was 186 U/ml with endotoxin from S. abortus equi and 137 U/ml with E. coli endotoxin.

C) Influence of apotransferrin complexes with zinc or copper ions on plasma endotoxin activity Human plasma from healthy donors was diluted 1:10 and inactivated by heating (80° C., 10 min.). Apotransferrin-zinc or apotransferrin-copper was then added. The concentration of apotransferrin-zinc in the plasma sample was 280 mg/dl and that of apotransferrin-copper 284 mg/dl. The same amount of albumin-zinc or albumin-copper was added to the reference plasma samples with the same zinc or copper concentration in each case. Endotoxin (Pseudomonas endotoxin and E. coli endotoxin) was then added to the plasma to which apotransferrin-zinc or apotransferrin-copper and albumin-zinc or albumin-copper had been added, to reach an endotoxin activity level of 300 EU/dl or 1,000 EU/dl in the plasma sample, which was then incubated for 60 minutes at 37° C. Following incubation, the endotoxin activity in the sample was measured using the Limulus test.

Plasma endotoxin activity was seen to be significantly reduced in the samples by addition of apotransferrin-zinc or apotransferrin-copper as compared to those to which only albumin (albumin-zinc or albumin-copper) was added.

a) Following incubation of endotoxin with albumin-zinc, plasma endotoxin activity was a maximum of approx. 4% lower than the activity level of the added endotoxin, at a zinc content of 4.8 μg/g of albumin (Zn(A)) as well as at a zinc content of 598 μg/g of albumin (Zn(B)). A nearly equivalent endotoxin activity reduction, approx. 4%, was recorded following incubation with albumin-copper with a copper content of 740 μg of copper per gram of albumin.

b) The addition of Atf,-Zn(A) to the plasma resulted in a reduction of endotoxin activity in plasma by 83.4%±4.2% (n=20) at an added concentration of 300 EU/dl of endotoxin and a reduction by 69.1% ±6.8% (n=18) at an added concentration of 1,000 EU/dl of endotoxin.

c) The addition of apotransferrin-zinc Atf.-Zn(B) with a zinc content of 598 μg of zinc per gram of apotransferrin to the plasma resulted in a reduction of plasma endotoxin activity following incubation by 93.9%±2.9% (n=20) at an added concentration of 500 EU/dl of endotoxin and a reduction by 94.8%±2.7% (n=20) at an added concentration of 1,000 EU/dl of endotoxin.

d) The addition of apotransferrin-copper Atf.-Cu(B) with a copper content of 740 μg of copper per gram of apotransferrin to the plasma resulted in a reduction of plasma endotoxin activity following incubation by 92.7% ±4.1% (n=16) at an added concentration of 500 EU/dl of endotoxin and a reduction by 90.8%±3.4% (n=16) at an added concentration of 1,000 EU/dl of endotoxin.

Summary Evaluation of Results

1.) Apotransferrin complexes with divalent zinc or copper ions are capable of reducing the biological activity of endotoxin, whereby the level of effectiveness depends on the apotransferrin-complex concentration used, and are therefore well-suited as an agent for prophylactic and therapeutic treatment of the toxic effects of endotoxins in the organism.

2.) Apotransferrin that is free of metal ions has only a slight effect on endotoxin activity.

3.) The degree to which apotransferrin-zinc or apotransferrin-copper reduces the toxic effects of endotoxin increases with the amount of zinc or copper bound by the apotransferrin. The zinc or copper content of the apotransferrin used should be at least 0.1 μg per gram of apotransferrin.

4.) The use of apotransferrin complexed with divalent zinc or copper ions instead of trivalent iron ions as an agent for treatment of the toxic effects of endotoxins in the organism results in endotoxin neutralization capacity nearly equivalent to that of transferrin and offers the great advantage that administration of these apotransferrin-metal complexes does not stimulate the formation of toxic oxygen are in the organism.

5.) The zinc ions added along with the apotransferrin-zinc complex as well as the copper ions in the apotransferrin-copper are capable of activating the enzyme "superoxide-dismutase" as well as a number of peroxidases. Thus the administration of apotransferrin-zinc or apotransferrin-copper has the decisive advantage over other prophylactic and therapeutic treatments of the toxic effects of endotoxins in the organism that, in addition to the neutralization of endotoxins, an improved elimination of the toxic oxygen radicals produced in large amounts in endotoxemia is achieved as well.

6.) Use of apotransferrin-zinc for endotoxin neutralization also has the advantage of not only achieving endotoxin neutralization, but of stimulating protein synthesis and thus, potentially, wound healing processes as well, since zinc ions facilitate DNA and RNA synthesis.

7.) The apotransferrin-zinc or apotransferrin-copper complexes can be combined with plasma protein solutions, whereby the immunoglobulin solutions may contain either IgG alone or the other plasma proteins as well, in particular IgM and IgA.

8.) The combination of apotransferrin-zinc and apotransferrin-copper with other plasma proteins, in particular with immunoglobulins of the IgG and IgM fractions, achieves a significantly greater reduction of the biological activity of endotoxins than does each individual component alone.

9.) The synergistic effect in neutralizing endotoxins makes the combination of apotransferrin-zinc and apotransferrin-copper particularly well-suited for therapeutic measures to reduce the toxic effects of endotoxin in all diseases in which an increased and prolonged transfer of endotoxins into the bloodstream is to be expected.

The various aspects of the invention are further described by the following examples:

EXAMPLE 1

The following experiments were carried out with apotransferrin-zinc to obtain an objective measure of the significance of the divalent zinc or copper ion load of apotransferrin for inactivation of endotoxin in plasma:

Human plasma from healthy donors was diluted 1:10 with 0.9% NaCl, then inactivated by heat (80° C., 5 minutes). Apotransferrin complexed with varying amounts of zinc was then added to the plasma. The apotransferrin concentration in these reaction preparations was 300 mg/dl. The zinc load of the apotransferrin was adjusted by adding varying amounts of $ZnCl_2$ to obtain apotransferrin-to-zinc mol ratios of 28:1, 1:1 and 1:3.

After the addition of apotransferrin-zinc to the inactivated plasma, endotoxin from E. coli in varying concentrations was also added to the plasma samples, resulting in endotoxin concentrations in the reaction preparation of 50, 100, 200, 300, 500, 750, 1,000 and 1,500 EU/dl. The preparation was incubated for 60 minutes at 37° C. immediately after the addition of endotoxin. Residual endotoxin activity in the samples was then measured. The inactivation capacity of the various apotransferrin-zinc solutions for an endotoxin excess of 10 EU/dl was then calculated on the basis of the values obtained in this way.

The inactivation capacity values for 100 mg/dl of apotransferrin-zinc were calculated as a function of apotransferrin-to-zinc mol ratios. The calculations were carried out so as to arrive at an endotoxin excess of 10 EU/dl:

a) 28:1:19.2 EU per 100 mg of apotransferrin-zinc
b) 1:1:87.1 EU per 100 mg of apotransferrin-zinc
c) 1:3:279.8 EU per 100 mg of apotransferrin-zinc Inactivation capacity can be increased by raising the proportion of zinc in the apotransferrin solution. For example, raising the zinc level from an apotransferrin-to-zinc mol ratio of 28:1 to 1:3 in the apotransferrin preparation increases inactivation capacity by a factor of 14.5. It is expected that, at a mol ratio of 1:3, the majority of apotransferrin molecules will have bound two molecules of zinc each.

EXAMPLE 2

To simulate the conditions occurring in therapy of gram-negative infections with antibiotics, an endotoxin increase in the blood was induced in animal experiments by first inoculating bacteria into the peritoneal cavity, then administering a bactericidal antibiotic intravenously, thus causing rapid bacterial decay. A blood collection catheter was inserted into the right jugular vein of anesthetized Wistar rats (250–300 g). A defined number of different species of bacteria was then inoculated into the animals' peritoneal cavity (E. coli, Klebsiella species and Pseudomonas aeruginosa, each in a concentration of $7.5 \times 10^5$ cfu per kg of b.w., i.e. a total of $2.3 \times 10^6$ cfu per kg of b.w.). 30 minutes after the bacteria were inoculated into the abdominal cavity the preparation under study (apotransferrin-zinc (Atf.-Zn(B) or apotransferrin-zinc in combination with immunoglobulin) was administered i.v. through the venous catheter by means of a perfusor in a dosage of 250 mg/kg b.w. The animals in the control group received a corresponding dosage of albumin-zinc in the same concentration and with the same zinc content i.v. In order to induce an endotoxemia, a bactericidal antibiotic (IMIPENEM=Zienam$^R$) was administered i.v. one hour after bacterial challenge. Blood samples for purposes of determining the endotoxin activity and the bacterial count in the blood were taken before bacterial inoculation as well as afterwards at 60-minute intervals over a total period of 6 hours following bacterial challenge.

The following preparations were administered i.v.: apotransferrin (Atf.-Zn(B)) with a zinc content of 598 μg of $Zn^{2+}$/g, and apotransferrin-zinc (Atf.-Zn(B)) combined with IgM (12%)-enriched 7S IgG (IgG-/A/M).

RESULTS a) When albumin-zinc was administered i.v., plasma endotoxin activity increased considerably following administration of the antibiotic. An average endotoxin activity of 234 EU/dl was reached as early as one hour after administration of the antibiotic. Five hours after antibiotic administration, mean plasma endotoxin activity had reached 278±31 EU/dl.

b) When apotransferrin-zinc (Atf.-Zn(B)) was administered i.v., the initial increase in plasma endotoxin activity—one hour after administration of the antibiotic—was reduced by approx. 68.3%±7.2% in comparison to the albumin control group. At the end of the experiment, i.e. five hours after administration of the antibiotic, endotoxin activity in the animals in the (Atf.-Zn(B)) group was still 63.5%±6.5% lower than in the albumin control group.

c) When apotransferrin (Atf.-Zn(A)) was administered i.v. in combination with an immunoglobulin (IgG-/A/M) enriched with 12% IgM the initial increase in plasma endotoxin activity—one hour after administration of the antibiotic—was reduced by approx. 73% in comparison to the albumin control group. Five hours after administration of the antibiotic, endotoxin activity in the animals that received this combination was still approx. 83.2%±7.9% lower than in the albumin control group.

The enhancement of inactivation capacity obtained with the combination of apotransferrin with immunoglobulins makes it possible to control a drastic increase in plasma endotoxin activity, even in cases where endotoxin continues to enter the bloodstream over a long period. Application of apotransferrin-zinc (Atf.-Zn(B)) alone results in a reduction of endotoxin activity, in the initial phase only, similar to that resulting from the apotransferrin-zinc/immunoglobulin combination. Unless either the dosage or the zinc load is raised, the inactivation capacity of apotransferrin-zinc alone will not suffice in cases of prolonged endotoxin passage into the blood, which may in turn lead to a resurgence of plasma endotoxin activity. The combination of immunoglobulin with apotransferrin-zinc represents a very efficient therapeutic alternative, even when apotransferrin-zinc with a zinc content under 500 μg/g of apotransferrin is used.

I claim:

1. Method of reducing blood endotoxin activity in a patient containing endotoxins comprising intravenously administering a therapeutically effective amount to reduce blood endotoxin activity employing apotransferrin bound to divalent zinc or copper cations forming an apotransferrin-zinc or apotransferrin-copper complex.

* * * * *